(12) United States Patent
Kim et al.

(10) Patent No.: US 8,877,217 B2
(45) Date of Patent: Nov. 4, 2014

(54) CATIONIC POLYMER NANOPARTICLES ENCAPSULATING AN ACTIVE INGREDIENTS, AND THE COSMETIC COMPOSITION CONTAINING THE SAME

(75) Inventors: Yong Jin Kim, Suwon-si (KR); Jin Woong Kim, Yongin-si (KR); Ju Hee Ryu, Seoul (KR); Jong Won Shim, Yongin-si (KR); Jun Oh Kim, Seongnam-si (KR); Ih Seop Chang, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 1639 days.

(21) Appl. No.: 12/090,680

(22) PCT Filed: Oct. 18, 2006

(86) PCT No.: PCT/KR2006/004238
§ 371 (c)(1),
(2), (4) Date: Apr. 18, 2008

(87) PCT Pub. No.: WO2007/046062
PCT Pub. Date: Apr. 20, 2007

(65) Prior Publication Data
US 2008/0268035 A1  Oct. 30, 2008

(30) Foreign Application Priority Data

Oct. 18, 2005 (KR) .................. 10-2005-0098057
Oct. 18, 2006 (KR) .................. 10-2006-0101316

(51) Int. Cl.
*A61K 8/11* (2006.01)
(52) U.S. Cl.
USPC ....................................... 424/401

(58) Field of Classification Search
None
See application file for complete search history.

(56) References Cited

U.S. PATENT DOCUMENTS

| 4,328,119 A * | 5/1982 | Iwasaki et al. ............. 264/4.7 |
| 6,183,774 B1 | 2/2001 | Aust et al. |
| 6,242,099 B1 * | 6/2001 | Grandmontagne et al. ............. 428/402.2 |
| 6,565,886 B1 | 5/2003 | Simonnet et al. |
| 2003/0232091 A1 * | 12/2003 | Shefer et al. .............. 424/490 |
| 2005/0181000 A1 * | 8/2005 | Lundquist et al. ........... 424/401 |

FOREIGN PATENT DOCUMENTS

| CN | 1687197 A * | 10/2005 | ........... A61K 47/34 |
| JP | 2003001100 A * | 1/2003 | ................... 424/401 |

OTHER PUBLICATIONS

CN2005-10018568 application, also published as CN1687197A. Zhuo, Renxi; Zhang, Ying. Amphiphilic triblock copolymer nanoparticle, its preparation and application, translation. The application was filed Apr. 18. 2005 and published Oct. 26, 2005.*
English translation of the abstract of JP2003001100A to inventor G. Haber, published Jan. 7, 2003.*

* cited by examiner

*Primary Examiner* — Audrea Buckley
(74) *Attorney, Agent, or Firm* — Sughrue Mion, PLLC (57) ABSTRACT

Disclosed herein are cationic polymer nanocapsules encapsulating an oil-soluble active ingredient, and a cosmetic composition containing the same. The cationic polymer nanocapsules have a molecular weight of 5,000-100,000, a surface potential of 5-100 mV and a particle size of 50-500 nm. Also, disclosed is a cosmetic composition containing said cationic polymer nanocapsules.

4 Claims, 3 Drawing Sheets

CATIONIC POLYMER NANOPARTICLES ENCAPSULATING AN ACTIVE INGREDIENTS, AND THE COSMETIC COMPOSITION CONTAINING THE SAME

This is a National Stage Application under 37 C.F.R. §371 of PCT/KR2006/004238 filed on Oct. 18, 2006 which claims priority from Korean Patent Application 10-2005-0098057 filed Oct. 18, 2005 and Korean Patent Application 10-2006-0101316 filed on Oct. 18, 2006, all of which are incorporated herein by reference.

TECHNICAL FIELD

The present invention relates to cationic polymer nanocapsules encapsulating an oil-soluble active ingredient and a cosmetic composition containing the same, and more particularly to cationic polymer nanocapsules having a molecular weight of 5,000-100,000, a surface potential of 5-100 mV and a particle size of 50-500 nm, as well as a cosmetic composition containing said cationic polymer nanocapsules.

BACKGROUND ART

The skin consists of three main layers: stratum corneum, epidermis and dermis. The skin is a primary defense barrier of the human body, which functions to protect various organs in the body from changes in temperature and humidity, and external environmental irritants such as UV and pollutants, this barrier function of skin depends on the physical and chemical properties of the stratum corneum present in the skin's outermost layer. The stratum corneum consists of keratinocytes, containing a keratin protein as a main component, and a lipid layer between the cells. It is known that, in the absorption of substances into the skin, the substances are actually very difficult through the keratinocytes, and are generally passed through the lipid layer between the keratinocytes. Thus, the skin absorption of fat-soluble substances such as tocopherol is relatively smooth, whereas substances difficult to distribute in the lipid layer, and high-molecular weight active ingredients, are not easy to absorb into the skin.

Till now, in order to increase the skin absorption of active ingredients having low skin absorption, many particle delivery systems, including nanoparticles employing high-molecular-weight copolymers, liposomes, deformable vesicles and nanoemulsions, have been studied. In the case of nanoparticles that use polyethylene/polycaprolactone copolymers containing Minoxidil, when they were applied to the skin of hairy guinea pigs and measure for the skin absorption thereof, it could be seen that the skin absorption thereof was higher than those of general liposome or 30% ethanol, containing the same amount of Minoxidil (J. Shim et al., J. Control. Release (2004) 97, 477).

Also, Korean Patent Laid-Open Publication No. 2005-0099213 discloses that each of a liposome, containing Rheum undulatum as a skin whitening active ingredient, and a solvent mixture (alcohol: butyleneglycol=7:3) containing the same amount of Rheum undulatum, was applied to the Franz permeation cell, and the skin absorption thereof with time was measured and, as a result, the skin absorption in the use of the liposome was 9-fold higher than in the use of the solvent.

Transfersome, a typical deformable vesicle, consists of phospholipid and a single-chain surfactant. In this case, it is thought that the single-chain surfactant increases the deformation of a lipid double layer by unstabilizing the lipid double layer and lowering the interfacial tension thereof. It was found that, when diclofenac as an arthritis therapeutic agent encapsulated in commercial hydrogel and transfersome was applied on the animal skin, the use of the transfersome had an improved ability to deliver the drug into the skin.

Thus, the retention time of the drug in intestinal organs was increased, so that the amount of the drug, required to obtain therapeutic effects, was reduced to 1/10 compared to the drug amount required in hydrogel (Cevc G, Blume G, Biochim. Biophys. Acta. (2001) 1514, 191).

Korean Patent Laid-Open Publication No. 2003-0069246 discloses a method for preparing a nanoemulsion having increased skin absorbability, which is prepared using a lecithin mixture of a controlled mixing ratio of saturated lecithin and unsaturated lecithin as a surfactant and contains one or more oils or physiologically active ingredients in the inner phase of nanoparticles and water in the outer phase.

These prior methods increased the skin absorption of active ingredients, but are not yet satisfactory or studied so as to be applicable to cosmetics.

Recently, studies have been actively conducted to stabilize oil-soluble active ingredients, which are widely used in cosmetics due to excellent effects such as skin wrinkle improvement and skin-moisturizing enhancement, but have problems in that they are easily discolored and degraded due to contact with external factors such as air or water and show a decrease in titer, leading to a reduction in effect. Among such active ingredients, retinol receives great attention due to excellent effects such as wrinkle-preventing effects, but is one of the most unstable components, which are easily broken by light, heat, air and water, and thus the use thereof is extremely limited.

Methods for stabilizing retinol in formulations to overcome such limitations will now be described in detail. EP Publication No. 440398 and PCT International Patent Publication No. 93/00085 disclose techniques for stabilizing retinol in the form of an oil-in-water emulsion by adding an antioxidant and a chelating agent. Also, U.S. Pat. No. 5,851,538 discloses porous microspheres for improving the stability of retinol and reducing skin irritation. In addition, U.S. Pat. No. 6,183,774 discloses a method for stabilizing retinol using cationic liposome, and U.S. Pat. No. 5,985,296 discloses a method for stabilizing retinol using cyclodextrin. Also, U.S. Pat. No. 6,565,886 discloses a method for stabilizing retinol using alkylene adipate nanocapsules. Such prior methods improved the stability of retinol, but are not yet satisfactory, and there is an urgent need to invent a system which can be widely used to stabilize oil-soluble active ingredients other than retinol.

Generally, in an attempt to increase the skin absorption of oil-soluble active ingredients, methods for reducing the size of capsules containing oil-soluble active ingredients are being widely studied. Thus, initial studies on microparticles have progressed to studies on nanoparticles. However, when polymer capsules having a particle size of less than 50 nm are applied on the skin together with cosmetics, they can cause a problem in terms of the human body safety, and the relative surface area of the capsules containing oil-soluble ingredients can be increased, leading to a decrease in the stability of the oil-soluble active ingredients.

Thus, there is an urgent need to invent a system which can be widely used to increase the skin absorption of various oil-soluble active ingredients.

DISCLOSURE

Technical Problem

Generally, in an attempt to increase the skin absorption of oil-soluble active ingredients, methods for reducing the size of capsules containing oil-soluble active ingredients are being widely studied. Thus, initial studies on microparticles have progressed to studies on nanoparticles. However, when polymer capsules having a particle size of less than 50 nm are applied on the skin together with cosmetics, there is a problem in that the relative surface area of the capsules containing oil-soluble active ingredients can be increased, leading to a decrease in the stability of the oil-soluble active ingredient.

Accordingly, the present inventors have studied to over the above-described problems occurring in the prior art and as a result, found that, when the surface charge state of nanocapsules themselves encapsulating oil-soluble active ingredients, rather than the particle size of the nanocapsules or the kind of polymers used in the preparation of the nanocapsules, is maintained in a specific range, they can increase the skin absorption of the oil-soluble active ingredients, thereby completing the present invention relating to cationic polymer nanocapsules having such surface potential and a cosmetic composition containing the same.

Thus, the present invention employs a double stabilization system, in which an oil-soluble active ingredient is adsorbed and encapsulated in a cationic functional group introduced into the moiety of a polymer, to induce a hydrogen bond between the cationic group and the oil-soluble active ingredient, so as to immobilize and stabilize the active ingredients in the capsules, thereby preventing leakage of the active ingredient, and the active ingredient is further stabilized in the particles using the outer polymer walls.

Technical Solution

Accordingly, the present invention conducted studies on a method of increasing the skin absorption of oil-soluble active ingredients using polymer nanoparticles and as a result, have found that the use of cationic polymer nanocapsules having a molecular weight of 5,000-100,000, a surface potential of 5-100 mV and a particle size of 50-500 nm increases the skin absorption of an oil-soluble active ingredient contained in the nanocapsules, thereby completing the present invention.

Therefore, it is an object of the present invention to provide cationic polymer nanocapsules capable of increasing the skin absorption of an oil-soluble active ingredient, as well as a preparation method thereof.

Another object of the present invention is to provide a cosmetic composition, which contains said cationic polymer nanocapsules and thus can increase the skin absorption of an oil-soluble active ingredient.

Advantageous Effects

The cationic polymer nanocapsules according to the present invention can provide an effective stabilization material which enables the initial activity of active ingredients to be maintained without change at the nanometer-sized particle level that can maximize the efficiency of active ingredients. Also, according to the present invention, a process for preparing the polymer nanocapsules for the delivery of an active ingredient can become significantly simpler.

DESCRIPTION OF DRAWINGS

The patent or application file contains at least one drawing executed in color. Copies of this patent or patent application publication with color drawing(s) will be provided by the Office upon request and payment of the necessary fee.

FIG. 2 shows the results of observation by confocal laser scanning microscopy (CLSM) for skin segments after skin absorption tests of test substances. In FIG. 2, (A): 40-nm polystyrene nanobeads; (B): 200-nm polystyrene nanobeads; and (C): polymer nanocapsules prepared in Example 1, containing nile red instead of coenzyme Q-10.

BEST MODE

To achieve the above objects, in one aspect, the present invention provides cationic polymer nanocapsules, which have a molecular weight of 5,000-100,000, a surface potential of 5-100 mV and a particle size of 50-500 nm and encapsulate an oil-soluble active ingredient therein.

In another aspect, the present invention provides a method for preparing cationic polymer nanocapsules, comprising the steps of: 1) preparing a hydrophobic functional polymer having a cationic functional group capable of adsorbing an oil-soluble active ingredient; 2) preparing cationic polymer nanocapsules capable of encapsulating the oil-soluble active ingredient; and 3) comparing various polymer capsules with respect to skin absorption.

In still another aspect, the present invention provides a cosmetic composition containing said cationic polymer nanocapsules.

Hereinafter, each step of one example of a method for preparing cationic polymer nanocapsules having a surface potential according to the present invention will be descried in detail.

1) Step of preparing hydrophobic polymer having cationic functional groups capable of adsorbing active ingredients:

In the present invention, the preparation of a polymer having cationic functional groups is conducted using an emulsifier-free emulsion polymerization process.

In the present invention, to impart cationic properties to the polymer, it is preferable to use radical-polymerizable cationic monomers, or low-molecular-weight polymers having a molecular weight of 400-800. Specific examples of these monomers and polymers may include 2-vinylpyridine, 3-vinylpyridine, 4-vinylpyridine, acrylamide, (meth)acrylamide, vinylpyrrolidone, vinyl-N-methylpyridinium chloride, 3-methacryloyl-2-ethyl-tetraalkylammonium chloride, methacryloyl-3-hydroxypropyltrimethylammonium chloride, acryloyl-2-ethyl-tetraalkylammonium chloride, acryloyl-3-propyltetraalkylammonium chloride, 3-methacryloyl-2-hydroxypropyltrimethylammonium chloride, methacryloyl-3-propyltetraalkylammonium chloride, (meth-acryloyl)ethyl dimethylamine and polyethyleneimine. Said monomers or low-molecular-weight polymers are used in an amount of 0.1-30 wt % based on the total weight of the polymer to be prepared. If the cationic groups are used in an amount of less than 0.1 wt %, water-dispersible nanoparticles will not be formed, and if they are added in an amount of more than 30 wt %, the monomers will be dispersed to an external water phase during polymerization, resulting in a decrease in yield.

An initiator, which is used in the present invention, is a cationic initiator, specific examples of which may include azo compounds, such as 2,2'-azobis(N,N'-dimethyleneisobutylamidine)dihydrochloride, 2,2'-azobis(2-methylpropionamidine)dihydro chloride, 2,2'-azobis(2-amidinopropane)dihydro chloride, 2,2'-azobis-2-methyl-N-[1,1-bis(hydroxymethyl)-2-hydroxymethyl]proppanamide, 2,2'-azobis-2-methyl-N-[1,1'-bis-(hydroxymethyl)-ethyl]propanamide, and 2,2'-azobis(isobutylamide)dehydrate. The initiator is preferably used in an amount of 0.9-1.1 wt % based on the total weight of polymer. If the initiator is used in an amount of less than 0.9 wt %, it will not show an effective initiation effect, and if it is used in an amount of more than 1.1 wt %, it will excessively increase polymerization rate, resulting in a decrease in the stability of the polymerization system.

The hydrophobic monomers, which are used in the present invention, are radical-polymerizable or ring-open-polymerizable monomers, specific examples of which may include styrene, p- or m-methylstyrene, p- or m-ethylstyrene, p- or m-chlorostyrene, p- or m-chlorostyrene, styrenesulfonic acid, lactate, glycolide, caprolactone, p- or m-t-butoxystyrene, methyl(meth)acrylate, ethyl(meth)acrylate, propyl(meth)acrylate, n-butyl(meth)acrylate, isobutyl(meth)acrylate, t-butyl(meth)acrylate, 2-ethylhexyl(meth)acrylate, n-octyl(meth)acrylate, lauryl(meth)acrylate, stearyl(meth)acrylate, 2-hydroxyethyl(meth)acrylate, polyethyleneglycol(meth)acrylate, methoxypolyethyleneglycol(meth)acrylate, glycidyl(meth)acrylate, dimethylaminoethyl(meth)acrylate, diethylaminoethyl(meth)acrylate, vinyl acetate, vinyl propionate, vinyl butyrate, vinyl ether, allyl butyl ether, allyl glycidyl ether, alkyl(meth)acrylamide and (meth)acrylonitrile.

2) Step of preparing cationic polymer nanocapsules encapsulating oil-soluble active ingredients:

A method for preparing the cationic polymer nanocapsules according to the present invention can be performed using a general nano precipitation method and comprises the following steps:

A step of dissolving oil-soluble active ingredients and the cationic polymer prepared in the step 1) in a suitable organic solvent, i.e., a highly volatile solvent (generally, alcohol/acetone), which is miscible with water and nontoxic and has a vapor pressure lower than that of water; a step of mixing the aqueous phase with the organic phase with stirring at a suitable rate to induce the self-association of the phases, thus preparing an emulsion; and evaporating the organic phase to prepare nanocapsules encapsulating the active ingredients present in the aqueous phase.

Examples of the oil-soluble active ingredients, which can be encapsulated in the nanocapsules, include retinol, retinylacetate, retinylpalmitate, $\alpha$-tocopherol, tocopherolacetate, tocopheryl linoleate, tocopheryl nicotinate, linoleic acid, coenzyme Q-10, resveratrol, plant extracts/essential oils, ursolic acid, oleanolic acid, oil soluble licorice and lipoic acid.

3) Step of comparing various polymer capsules with respect to skin absorption:

In the present invention, cationic polymer nanocapsules prepared through the steps 1) and 2) and various polymer nanocapsules were subjected to a test for comparing skin absorption rates, whereby the characteristic of polymer nanocapsules, which could maximize skin absorption rate, could be found.

To measure the skin absorption of active ingredients in the use of the polymer nanocapsules according to the present invention, for example, the skin absorption of coenzyme Q-10 was measured on the skin of guinea pigs using the Franz permeation cell, but the present invention is not necessarily limited thereto.

The test process will now be briefly described. Just before the test, the abdominal skin of guinea pigs was collected and cut into areas of 1 cm$^2$. The cut skin was placed on the permeation cell having a diameter of 0.9 cm and fixed with a clamp. Then, one side of the fixed skin was applied with 0.5 ml of each of compositions (Examples 1-4 and Comparative Example 1-4) to be measured, and the other side of the skin was brought into contact with purified water. The test temperature was maintained at 32° C. (actual skin temperature), and at 18 hours after the start of the test, some of purified water at the opposite side was collected and the amount of coenzyme-10, which permeated the skin, was measured in the collected water using HPLC. Also, to measure the amount of coenzyme Q-10 absorbed into the skin of guinea pigs, coenzyme Q-10 was extracted from the skin tissue using methanol, and the amount of coenzyme was measured using HPLC.

Various polymer capsules were compared with respect to skin absorption according to the above-described method and, as a result, found that the skin absorption of oil-soluble active ingredients contained in the nanocapsules was the highest in the case of cationic polymer nanocapsules having a molecular weight of 5,000-100,000, a surface potential of 5-100 mV and a particle size of 50-500 nm.

If the molecular weight of the cationic polymer nanocapsules is less than 5,000, the solubility of the nanocapsules in an organic solvent will be lower than in the case of a molecular weight of more than 5,000, and on the contrary, the solubility in water will be increased, thus imposing limitations on the efficient preparation of particles. On the other hand, if the molecular weight is more than 100,000, aggregation will frequently occur, imposing limitations on the efficient preparation of particles.

If the surface potential of the cationic polymer nanocapsules according to the present invention is less than 5 mV, the nanocapsules will have insignificant skin absorption rate, and if it is more than 100 mV, the aggregation of water-soluble components and water-soluble polymers in formulations will occur, extremely limiting the use of the nanocapsules.

Meanwhile, if the particle size of the polymer nanocapsules is less than 50 nm, the stability of the oil-soluble active ingredients can be decreased, and if the particle size of the polymer nanocapsules is more than 500 nm, the nanocapsules will not be easily absorbed into the skin, making it difficult to expect the efficacy of the oil-soluble active ingredients encapsulated in the nanocapsules.

Said preparation method is one example of the method for preparing the inventive cationic polymer nanocapsules having a molecular weight of 5,000-100,000, a surface potential of 5-100 mV and a particle size of 50-500 nm, but the scope of the present invention is not necessarily limited thereto.

Moreover, the present invention relates to a cosmetic composition, which contains said cationic polymer nanocapsules, and thus can maximize the skin absorption of oil-soluble active ingredients.

Thus, the cosmetic composition according to the present invention can contain cationic polymer nanocapsules, which have a molecular weight of 5,000-100,000, a surface potential of 5-100 mV and a particle size of 50-500 nm and, at the same time, cationic functional groups.

Also, the cosmetic composition according to the present invention can contain the cationic polymer nanocapsules prepared through said steps 1) and 2).

Although the content range of the cationic polymer nanocapsules according to the present invention is not specified in the case of cosmetic compositions, the cationic polymer nanocapsules are preferably contained in an amount of 0.1-10 wt % in order to adjust the content of functional products. If the content of the nanoparticles is more than 10 wt %, it will be difficult to adjust the sensory feel of functional products, and if it is less than 0.1 wt %, it will be difficult to adjust the total content of functional products, thus making it difficult to formulate the nano capsules.

The cosmetic composition can be formulated into, for example, skin lotion, milk lotion, massage cream, nourishing cream, pack, gel, essence, lipstick, makeup base, foundation, lotion, ointment, cream, patch and spray, but the scope of the present invention is not limited thereto.

MODE FOR INVENTION

Hereinafter, the present invention will be described in further detail with reference to examples. It is to be understood, however, that these examples are for illustrative purposes only and are not to be construed to limit the scope of the present invention.

Example 1

A butylmethacrylate random copolymer was prepared in the following manner. 75 wt %, based on the weight of the polymer, of butylmethacrylate was mixed with 25 wt % of (methacryloyl)ethyl diethylamine. The mixture was added to a 0.5% aqueous solution of 2,2'-azobis(2-methylpropionamidine)dihydrochloride and polymerized at 70° C. for 4 hours in a nitrogen atmosphere with stirring at 250 rpm, thus obtaining a polymer latex. The produced polymer was precipitated with sodium chloride to obtain powder. The powder was recrystallized with acetone/water to remove unreacted monomers, and precipitated again with sodium chloride to obtain powder. The powder was filtered and washed with water and this filtration and washing process was repeated several times. The resulting material was dried in a vacuum oven, thus obtaining capsules as powder.

To prepare nanocapsules encapsulating coenzyme Q-10, 2 g of the polymer having cationic functional groups, prepared in said process, and 1 g of coenzyme Q-10(NISSHIN PHARMA, Japan), were dissolved in 100 ml of ethanol. While 200 ml of distilled water was stirred in a flask, the above-prepared mixture of polymer/coenzyme Q-10/ethanol was added thereto to obtain a self-associated material. From the produced material, ethanol and a small amount of water were evaporated using a rotary evaporator, thus obtaining 50 ml of an aqueous polymer solution.

Example 2

A polymer and capsules were prepared in the same manner as in Example 1, except that methylmethacrylate was used to prepare a methylmethacrylate random copolymer having cationic functional groups.

Example 3

A polymer and capsules were prepared in the same manner as in Example 1, except that polystyrene was used to prepare a polystyrene random copolymer having cationic functional groups.

Example 4

A poly(lactic-co-glycolic acid) (PLGA) random copolymer having cationic functional groups was prepared in the following manner. First, 0.37 mmol of a PLGA polymer and 1.2 mmol of dicyclohexylcarboimide were dissolved in 10 ml of an anhydrous dimethylformamide solution and allowed to react for 4 hours. Then, 4 mmol of polyethyleneimine (PEI) was added to the poly(lactic-co-glycolic acid)/dimethylformamide solution and allowed to react. After 1 hour, the reaction solution was added to a diethylether solution to obtain a precipitate, thus preparing a PLGA-PEI copolymer.

Comparative Example 1

Capsules were prepared in the same manner as in Example 1, except that, in the preparation of the polymer, the cationic functional groups were not introduced, SLS (sodium lauryl sulfate) was use in an amount of 10 wt % based on the weight of the polymer, and only butylmethacrylate was used as a monomer for polymerization.

Comparative Example 2

Capsules were prepared in the same manner as in Example 1, except that, in the preparation of the polymer, the cationic functional groups were not introduced, SLS (sodium lauryl sulfate) was use in an amount of 10 wt % based on the weight of the polymer, and only methylmethacrylate was used as a monomer for polymerization.

Comparative Example 3

Capsules were prepared in the same manner as in Example 3, except that, in the preparation of the polymer, the cationic functional groups were not introduced, SLS (sodium lauryl sulfate) was use in an amount of 10 wt % based on the weight of the polymer, and only styrene was used as a monomer for polymerization.

Comparative Example 4

Capsules were prepared in the same manner as in Example 4, except that, in the preparation of the polymer, the cationic functional groups were not introduced, SLS (sodium lauryl sulfate) was use in an amount of 10 wt % based on the weight of the polymer, and only poly(lactic-co-glycolic acid) was used as a monomer for polymerization.

Test Example 1

Measurement of Surface Charge of Polymer Capsules

The zeta potential of the product prepared in each of Examples 1-4 and Comparative Examples 1-4 was measured using Zetasizer 3000HS (Malvern, UK) in a neutral condition (pH=7), and the measurement results are shown in Table 1 below.

As shown in Table 1, it can be seen that the samples of Examples 1-4, in which cationic functional groups were introduced in the polymerization process, showed positive surface charges. On the other hand, the samples of Comparative Examples 1-4, in which the capsules were made of only the polymers without introducing the cationic functional groups in the polymerization process, showed positive surface charges.

Test Example 2

Measurement of Particle Size of Polymer Capsules by Dynamic Light Scattering

The particle size of the product prepared in each of Examples 1-4 and Comparative Examples 1-4 was measured while maintaining a scattering angle of 90° and a temperature of 25° C., and the measurement results are shown in Table 1 below.

TABLE 1

| Samples | Particle size (nm) | Zeta potential (mV) |
|---|---|---|
| Example 1 | 193 | +61.4 |
| Example 2 | 307 | +60.5 |
| Example 3 | 201 | +58.5 |
| Example 4 | 225 | +10.3 |
| Comparative Example 1 | 71 | −59.7 |
| Comparative Example 2 | 38 | −62.0 |
| Comparative Example 3 | 48 | −58.5 |
| Comparative Example 4 | 57 | −57.3 |

Test Example 3

Observation of Morphology of Polymer Nanocapsules

Figure 1:
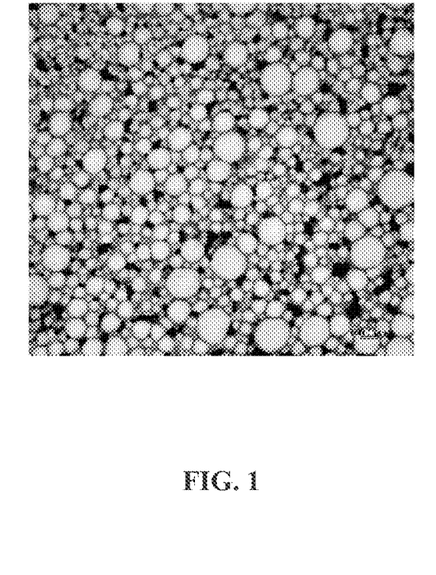
FIG. 1 is a transmission electron microscope of butyl-methacrylate polymer nanocapsules (Example 1), containing coenzyme Q-10 and having cationic functional groups.

The morphology of the cationic polymer nanoparticles prepared in Example 1 was observed with a transmission electron microscope (TEM), and the observation results are shown in FIG. 1.

As can be seen that FIG. 1, it was observed that the inventive nanocapsules prepared in Example 1 had a spherical shape. FIG. 1 is a transmission electron microscope photograph showing the results of observation of the cationic polymer nanocapsules containing coenzyme Q-10, prepared in Example 1 of the present invention.

Test Example 4

Measurement of in vitro skin absorption of polymer nanocapsules

The skin absorption of coenzyme Q-10 was measured on guinea pig using the Franz permeation cell. Just before the test, the abdominal skin of guinea pigs was collected and cut into an area of 1 cm$^2$. The cut skin was placed on the permeation cell having a diameter of 0.9 cm and fixed with a clamp. Then, one side of the fixed skin was applied with 0.5 ml of each of Examples 1-4 and Comparative Example 1-4, and the other side of the skin was brought into contact with purified water. The test temperature was maintained at 32° C. (actual skin temperature), and at 18 hours after the start of the test, some of purified water at the opposite side was collected and the amount of coenzyme-10, which permeated the skin, was measured in the collected water using HPLC.

Also, to measure the amount of coenzyme Q-10 absorbed into the skin of guinea pigs, coenzyme Q-10 was extracted from the skin tissue using methanol, and the amount of coenzyme Q-10 was measured using HPLC. The measurement results are shown in Table 2 below.

TABLE 2

| Skin absorption (μg) | | | |
|---|---|---|---|
| Example 1 | 6.05 | Comparative Example 1 | 3.95 |
| Example 2 | 6.74 | Comparative Example 2 | 1.86 |
| Example 3 | 5.78 | Comparative Example 3 | 0.98 |
| Example 4 | 3.56 | Comparative Example 4 | 1.21 |

As can be seen in Table 2 above, the skin absorption of the samples of Examples 1-4, in which the cationic functional groups were introduced in the preparation of the polymers, was 1.5-4.9 fold increased compared to that of Comparative Examples 1-4, in which the capsules were made of only the polymers without introducing the cationic functional groups in the preparation of the polymers.

Test Example 5

Measurement of in Vivo Skin Absorption of Polymer Nanocapsules

To measure in vivo skin absorption, a small amount of nile red was added instead of coenzyme Q-10 during the preparation of the capsules in Example 1. The nanocapsules thus prepared had a mean particle size of 140 nm. For use as control groups for comparatively evaluating the in vivo skin absorption of the prepared nanocapsules, polystyrene nanobeads having a surface potential of −2 mV and particle sizes of 40 nm and 200 nm were purchased from Molecular Probes Co. The purchased polystyrene nanobeads had a fluorescent substance encapsulated therein, which allowed the observation of skin absorption by fluorescence.

Before treatment with the two polystyrene nanobead control groups and Example 1, the hair of the back of guinea pigs was removed. Then, the back of the guinea pigs was patched with each of said samples. After 24 hours of the patching, the skin was cut with a 6-mm skin cutting punch. The cut skin was washed at least four times with purified water and then frozen below 26° C. in an O.C.T. compound. Then, the frozen skin was sliced at a thickness of 10-18 μm and placed on a slide glass. After washing out the remaining O.C.T. compound, the tissue was covered with a cover glass, and then immediately, observed with a confocal laser scanning microscope (CLSM). The observation results are shown in FIG. 2.

Figure 2:
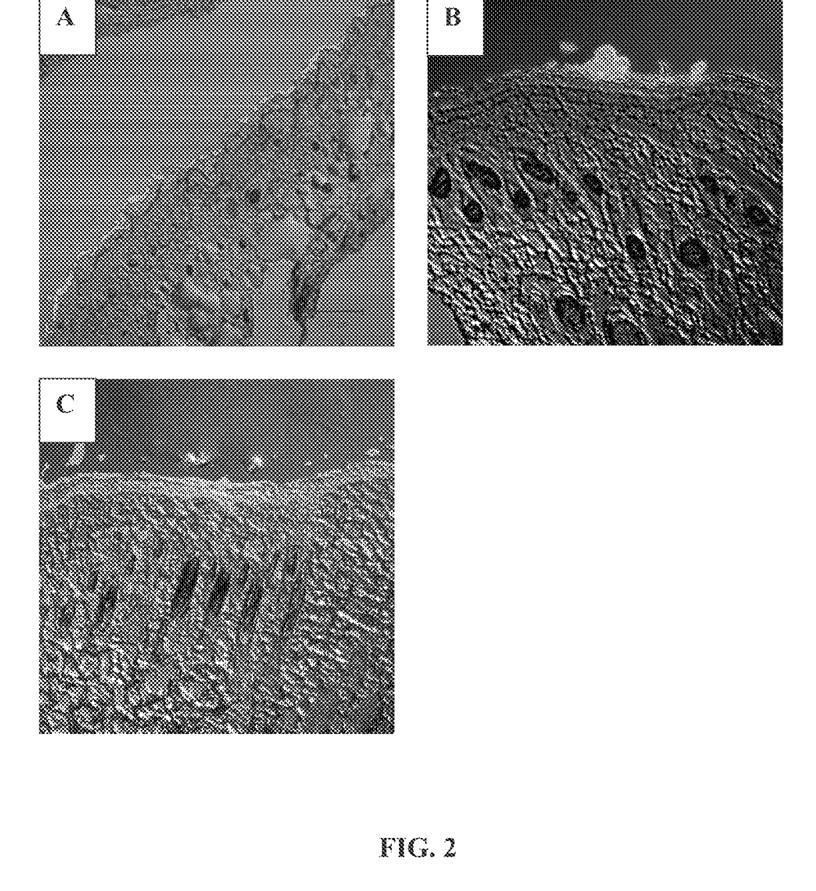

FIG. 2 is a photograph showing the results of confocal laser scanning observation of skin sections, conducted after the skin absorption tests of the polystyrene nanobeads having diameters of 40 nm and 200 nm, and the polymer nanocapsules having cationic functional groups (Example 1).

As shown in FIG. 2, the polymer nanoparticles (FIG. 2C) prepared in Example 1 of the present invention showed significantly excellent skin absorbability in spite of a particle size of 140 nm, compared to the 40-nm polystyrene nanobeads (FIG. 2A), the fluorescence of which was observed only on the surface of the skin. Also, in case of the 200-nm polystyrene nanobeads (FIG. 2B), fluorescence was observed only on the surface of the skin.

From the results of the images observed by the confocal laser scanning microscope, it was found that, in the case of the 40-nm and 200-nm polystyrene nanobeads, fluorescence was observed only on the skin surface, whereas, in the case of the polymer nanocapsules prepared in Example 1, fluorescence was observed in most of the epidermal layer. Through this Test Example, it was found that the surface charge of the polymer nanocapsules greatly influenced the increase in the skin absorption of oil-soluble active ingredients.

Formulation 1

The composition of Table 3 was used to prepare Formulation 1 as a clear gel-type soluble formulation. The formulation had a viscosity of about 4,000 cps, as measured with spindle No. 3 using Brookfield (LVDVII+) at 30° C. and 12 rpm.

TABLE 3

| Components | Content (wt %) |
| --- | --- |
| Glycerin | 5 |
| Propylene glycol | 4 |
| Nanocapsule dispersion of Example 1 | 5 |
| Ethanol | 10 |
| Sodium polyacrylate | 0.5 |
| Preservative | q.s. |
| Purified water | Balance |

Formulation 2

The composition of Table 4 was used to prepare Formulation 2 as an emulsion formulation. Each of the oil and aqueous phases was completely dissolved at 70° C., and emulsified at 7,000 rpm for 5 minutes, thus preparing opaque gel-type lotion. The lotion had a viscosity of about 7,000 cps.

TABLE 4

| | Components | Content (wt %) |
| --- | --- | --- |
| Oil phase | Stearic acid | 2 |
| | Cetyl alcohol | 2 |
| | Lanolin alcohol | 2 |
| | Liquid paraffin | 7 |
| | Cyclomethicone | 5 |
| | Polyoxyethylene monooleic acid ester | 2 |
| | Preservative/antioxidant | q.s. |
| Aqueous phase | Glycerin | 3 |
| | Propylene glycol | 5 |
| | Triethylamine | 1 |
| | Nanocapsule dispersion of Example 1 | 10 |
| | Sodium polyacrylate | 0.15 |
| | Purified water | Balance |

Formulation 3

The composition of Table 5 was used to prepare Formulation 3 as a cream formulation. The preparation process was the same as in Formulation 2.

TABLE 5

| | Components | Content (wt %) |
| --- | --- | --- |
| Oil phase | Beeswax | 2 |
| | Stearylalcohol | 5 |
| | Stearic acid | 8 |
| | Squalane | 10 |
| | Popyleneglycolmonostearate | 3 |
| | Polyoxyethylenecetylether | 1 |
| | Preservative/antioxidant | q.s |
| Aqueous phase | Propylene glycol | 8 |
| | Glycerin | 4 |
| | Triethylamine | 1 |
| | Nanocapsule dispersion of Example 1 | 10 |
| | Purified water | Balance |

Test Example 6

Examination of Stability of Gel Formulation

To examine the stability of the formulation containing the prepared capsules, Formulation 1 was stored in each of a freezer at −4° C. and a constant temperature chamber at room temperature and 40° C., and after 4 weeks, the sample was taken and observed. As a result, the formulation containing the prepared capsules was observed to be stable without phase separation.

Test Example 7

Examination of Stability of Emulsion Formulation

To examine the stability of the formulation containing the prepared capsules, Formulation 2 was stored in each of a freezer at −4° C. and a constant temperature chamber at room temperature and 40° C., and after 4 weeks, the sample was taken and observed. As a result, the formulation containing the prepared capsules was observed to be stable without phase separation.

Test Example 8

Examination of Stability of Cream Formulation

To examine the stability of the formulation containing the prepared capsules, Formulation 3 was stored in each of a freezer at −4° C. and a constant temperature chamber at room temperature and 40° C., and after 4 weeks, the sample was taken and observed. As a result, the formulation containing the prepared capsules was observed to be stable without phase separation.

As can be seen from the above results, it was observed that the cationic polymer nanocapsules prepared in Examples 1-4 did not reduce the stability of the cosmetic formulations.

Example 5

Capsules were prepared in the same manner as in Example 1, except that retinol was used as active ingredient.

Example 6

Capsules were prepared in the same manner as in Example 1, except that oil-soluble licorice was used as active ingredient.

Comparative Example 5

Capsules were prepared in the same manner as in Example 1, except that butylmethacrylate was introduced in the preparation of the polymer.

Formulation 1 and Comparative Formulation 1

The composition of Table 6 below was used to prepare Formulation 4 and Comparative Formulation 1 as clear gel-type solubilized formulations. The formulations had a viscosity of about 4,000 cps, as measured using Brookfield (LVD-VII+) at 30° C. and 12 rpm.

TABLE 6

| Components (wt %) | Formulation 4 | Comparative Formulation 1 |
| --- | --- | --- |
| Glycerin | 5 | 5 |
| Propylene glycol | 4 | 4 |
| Nanocapsule dispersion of Example 5 | 5 | — |
| Nanocapsule dispersion of Comparative Example 5 | — | 5 |
| Ethanol | 10 | 10 |
| Sodium polyacrylate | 0.5 | 0.5 |
| Preservative | q.s. | q.s. |
| Purified water | Balance | Balance |

Formulation 5 and Comparative Formulation 2

The composition of Table 7 below was used to prepare Formulation 5 and Comparative Formulation 2 as emulsion formulations. Each of the oil and aqueous phases was completely dissolved at 70° C. and emulsified at 7,000 rpm for 5 minutes, thus preparing opaque gel-type lotion. The lotion had a viscosity of about 2,500 cps.

TABLE 7

| | Components (wt %) | Formulation 5 | Comparative Formulation 2 |
|---|---|---|---|
| Oil phase | Stearic acid | 2 | 2 |
| | Cetyl alcohol | 2 | 2 |
| | Lanoline alcohol | 2 | 2 |
| | Liquid paraffin | 7 | 7 |
| | Cyclomethicone | 5 | 5 |
| | Polyoxyethylene monooleic acid ester | 2 | 2 |
| | Preservative/antioxidant | q.s. | q.s. |
| Aqueous phase | Glycerin | 3 | 3 |
| | Propylene glycol | 5 | 5 |
| | Triethylamine | 1 | 1 |
| | Nanocapsule dispersion of Example 5 | 10 | — |
| | Nanocapsule dispersion of Comparative Example 5 | — | 10 |
| | Sodium polyacrylate | 0.15 | 0.15 |
| | Purified water | Balance | Balance |

Formulation 6 and Comparative Formulation 3

The composition of Table 8 was used to prepare Formulation 6 and Comparative Formulation 3 as cream formulations. The preparation process was the same as in Formulation 5.

TABLE 8

| | Components (wt %) | Formulation 6 | Comparative Formulation 3 |
|---|---|---|---|
| Oil phase | Beeswax | 2 | 2 |
| | Stearylalcohol | 5 | 5 |
| | Stearic acid | 8 | 8 |
| | Squalane | 10 | 10 |
| | Propyleneglycolmonostearate | 3 | 3 |
| | Polyoxyethylene cetylether | 1 | 1 |
| | Preservative and antioxidant | q.s. | q.s. |
| Aqueous phase | Propylene glycol | 8 | 8 |
| | Glycerin | 4 | 4 |
| | Triethylamine | 1 | 1 |
| | Nanocapsule dispersion of Example 5 | 10 | — |
| | Nanocapsule dispersion of Comparative Example 5 | — | 10 |
| | Purified water | Balance | Balance |

Test Example 9

Figure 3:
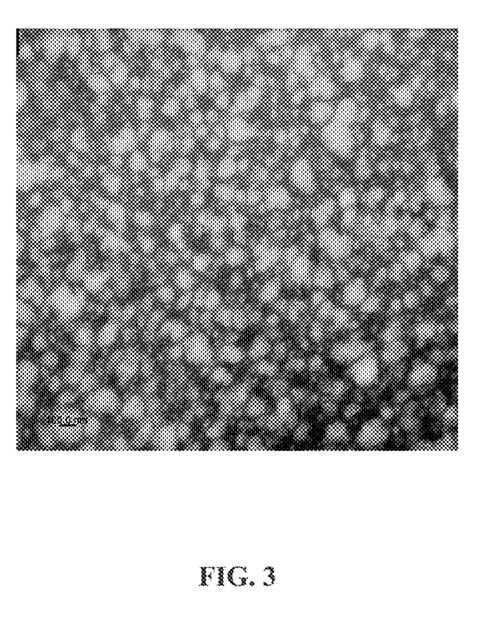
FIG. 3 is a transmission electron microscope of butyl-methacrylate polymer nanocapsules (Example 5), containing retinol and having cationic functional groups.

The morphology of the two-phase cationic polymer nanoparticles prepared in Example 5 was observed using a transmission electron microscope (TEM). The observation results are shown in FIG. 3 below. From the results of FIG. 3, it could be seen that the polymer nanocapsules prepared in Example 5 consisted spherical polymer particles.

Test Example 10

To examine the stability of the prepared capsules, Formulation 4 and Comparative Formulation 1 were stored in an oven at each of room temperature and 40° C. After a given period of time, the samples were taken, and the amount of the remaining active ingredient in each of the samples was measured using liquid chromatography. The measurement results are shown in Table 9.

TABLE 9

| | | Retention rate (%) of initial concentration | | | |
|---|---|---|---|---|---|
| Capsules | Storage temperature (° C.) | After 1 day | After 7 days | After 14 days | After 28 days |
| Retinol-containing capsules of Example 5 (Formulation 4) | Room temperature | 100 | 100 | 100 | 100 |
| | 40 | 100 | 100 | 100 | 100 |
| Retinol-containing capsules of Comparative Example 5 (Comparative Formulation 1) | Room temperature | 100 | 95 | 92 | 89 |
| | 40 | 100 | 92 | 89 | 78 |
| Form introduced directly with retinol | Room temperature | 98 | 95 | 88 | 63 |
| | 40 | 89 | 65 | 52 | 33 |

As can be seen in Table 9, in the solubilized formulation of Formulation 4, retinol present in the cationic polymer capsules had excellent stability.

Test Example 11

To examine the stability of the prepared emulsion formulation, Formulation 5 and Comparative Formulation 2 were stored in an oven at each of room temperature and 40° C. After a given period of time, the samples were taken and the amount of the remaining active ingredient in each of the samples was measured, and the measurement results are shown in Table 10 below.

TABLE 10

| | | Retention rate (%) of initial concentration | | | |
|---|---|---|---|---|---|
| Capsules | Storage temperature (° C.) | After 1 day | After 7 days | After 14 days | After 28 days |
| Retinol-containing capsules of Example 5 (Formulation 5) | Room temperature | 100 | 100 | 100 | 100 |
| | 40 | 100 | 100 | 100 | 96 |
| Retinol-containing capsules of Comparative Example 5 (Comparative Formulation 2) | Room temperature | 100 | 96 | 90 | 80 |
| | 40 | 99 | 92 | 83 | 75 |
| Form introduced directly with retinol | Room temperature | 99 | 92 | 85 | 61 |
| | 40 | 88 | 66 | 55 | 38 |

As can be seen in Table 10 above, in the emulsion formulation of Formulation 5, retinol present in the nanocapsules had excellent stability. This suggests that the cationic polymer nanocapsules according to the present invention is an excellent double-stabilization system, in which retinol as an active ingredient is encapsulated with cationic functional groups to maintain the chemical structure thereof, and retinol is prevented from leaking out of the capsules is prevented, and is protected from an external harmful environment by the polymer matrix.

Test Example 12

To examine the stability of the prepared cream formulation, the samples of Formulation 6 and Comparative Formulation were stored in an oven at each of room temperature and 40° C. After a given period of time, the samples were taken and the amount of the remaining active ingredient in each of the samples was measured using liquid chromatography, and the measurement results are shown in Table 11.

TABLE 11

| Capsules | Storage temperature (° C.) | Retention rate (%) of initial concentration | | | |
|---|---|---|---|---|---|
| | | After 1 day | After 7 days | After 14 days | After 28 days |
| Retinol-containing capsules of Example 5 (Formulation 6) | Room temperature | 100 | 100 | 100 | 100 |
| | 40 | 100 | 100 | 99 | 98 |
| Retinol-containing capsules of Comparative Example 5 (Comparative Formulation 3) | Room temperature | 100 | 98 | 92 | 88 |
| | 40 | 93 | 97 | 85 | 79 |
| Form introduced directly with retinol | Room temperature | 98 | 93 | 78 | 60 |
| | 40 | 85 | 67 | 51 | 40 |

As can be seen in Table 11, in the cream formulation, the cationic functional groups greatly contributed to the stabilization of retinol in the formulation, as in the case of the lotion formulation.

Test Example 13

To examine the stabilities of other components in the inventive composition, each of Examples 6 and 1 was used instead of Example 5 to prepare Formulation 6. The stability of the prepared formulation was tested in the same manner as in Test Example, and the measurement results are shown in Table 12 below.

TABLE 12

| Capsules | Storage temperature (° C.) | Retention rate (%) of initial concentration | | | |
|---|---|---|---|---|---|
| | | After 1 day | After 7 days | After 14 days | After 28 days |
| Formulation containing nanocapsules of Example 6 | Room temperature | 100 | 99 | 99 | 100 |
| | 40 | 100 | 99 | 97 | 96 |
| Formulation containing nanocapsules of Example 1 | Room temperature | 100 | 100 | 99 | 99 |
| | 40 | 100 | 98 | 96 | 94 |

As can be seen in Table 12, the cationic polymer nanocapsules also had an excellent effect on the stabilization of other oil-soluble components.

As described above, retinol in simple polymers did not show excellent stability, because it would be brought into contact with an external environment due to the swelling of the particles, caused by water, oil or surfactants in cosmetic formulations. Also, the cationic polymer nanocapsules prepared in Comparative Example 5 showed excellent stability in the formulations, compared to the other systems, because the cationic groups of the polymer particles stabilized the chemical structure of retinol and had an increased ability to capture retinol by adsorption so as to prevent retinol from leaking out of the capsules. However, in the cationic polymer nanocapsules prepared in Example 5, the swelling of the particles, caused by water or oil in the formulation, was reduced due to the cationic groups that adsorbed retinol, together with the polymer matrix walls, and thus, external stimulation was more effectively blocked.

The invention claimed is:

1. A cosmetic composition comprising cationic polymer nanocapsules which have a molecular weight of 5,000-100,000, a surface potential of 5-100 mV and a particle size of 50-500 nm, and encapsulate an oil-soluble active ingredient therein;
    wherein the oil-soluble ingredient is one or more selected from the group consisting of retinal, retinylacetate, retinylpalmitate, a-tocopherol, tocopherolacetate, tocopheryl linoleate, tocopheryl nicotinate, linoleic acid, coenzyme Q-10, resveratrol, plant extracts, essential oils, ursolic acid, oleanolic acid, oil-soluble licorice and lipoic acid;
    wherein the cationic polymer nanocapsules are formed from a hydrophobic monomer selected from the group consisting of styrene, p- or m-methylstyrene, p- or m-ethylstyrene, p- or m-chlorostyrene, p- or m-chlorostyrene, styrenesulfonic acid, lactate, glycolide, caprolactone, p- or m-t-butoxystyrene, methyl(meth)acrylate, ethyl(meth)acrylate, propyl(meth)acrylate, n-butyl(meth)acrylate, isobutyl(meth)acrylate, t-butyl(meth)acrylate, 2-ethylhexyl(meth)acrylate, n-octyl(meth)acrylate, lauryl(meth)acrylate, stearyl(meth)acrylate, 2-hydroxyethyl(meth)acrylate, polyethyleneglycol(meth)acrylate, methoxypolyethyleneglycol(meth)acrylate, glycidyl(meth)acrylate, dimethylaminoethyl(meth)acrylate, diethylaminoethyl(meth)acrylate, vinyl acetate, vinyl propionate, vinyl butyrate, vinyl ether, allyl butyl ether, allyl glycidyl ether, alkyl(meth)acrylamide and (meth)acrylonitrile
    and wherein the cationic polymer nanocapsules are present in said composition in an amount of 0.1-10 wt % based on the total weight of the composition.

2. The cosmetic composition of claim 1, wherein the cationic polymer nanocapsules are used to increase the skin absorption of the active ingredient.

3. The cosmetic composition of claim 1, wherein the cationic polymer nanocapsules are used to stabilize the oil-soluble active ingredient.

4. The cosmetic composition of claim 1, wherein the cationic polymer nanocapsules are present in said composition in an amount of 5-10 wt % based on the total weight of the composition.

* * * * *